(12) United States Patent
Schmelzer

(10) Patent No.: US 7,736,627 B2
(45) Date of Patent: *Jun. 15, 2010

(54) HFA SUSPENSION FORMULATIONS CONTAINING AN ANTICHOLINERGIC

(75) Inventor: Christel Schmelzer, Ingelheim am Rhein (DE)

(73) Assignee: Boehringer Ingelheim Pharma GmbH & Co. KG, Ingelheim (DE)

( * ) Notice: Subject to any disclaimer, the term of this patent is extended or adjusted under 35 U.S.C. 154(b) by 178 days.

This patent is subject to a terminal disclaimer.

(21) Appl. No.: 11/876,162

(22) Filed: Oct. 22, 2007

(65) Prior Publication Data

US 2008/0044361 A1 Feb. 21, 2008

Related U.S. Application Data

(63) Continuation of application No. 10/392,559, filed on Mar. 20, 2003, now Pat. No. 7,311,894.

(60) Provisional application No. 60/386,145, filed on Jun. 5, 2002.

(30) Foreign Application Priority Data

Mar. 28, 2002 (DE) ................. 102 14 263

(51) Int. Cl.
*A61K 9/12* (2006.01)
*A61K 9/14* (2006.01)
(52) U.S. Cl. .................... 424/45; 424/46; 424/434; 514/291; 514/629
(58) Field of Classification Search ........... 424/45, 424/46, 434; 514/291, 629
See application file for complete search history.

(56) References Cited

U.S. PATENT DOCUMENTS

| | | | |
|---|---|---|---|
| 4,042,700 A | 8/1977 | Banholzer et al. | |
| 4,608,377 A | 8/1986 | Banholzer et al. | |
| 4,783,534 A | 11/1988 | Banholzer | |
| 5,610,163 A | 3/1997 | Banholzer et al. | |
| 5,654,314 A | 8/1997 | Banholzer et al. | |
| 5,770,738 A | 6/1998 | Banholzer et al. | |
| 5,952,505 A | 9/1999 | Banholzer | |
| 5,955,058 A | 9/1999 | Jager et al. | |
| 6,045,778 A | 4/2000 | Jager et al. | |
| 6,475,467 B1 | 11/2002 | Keller et al. | |
| 6,486,321 B2 | 11/2002 | Banholzer et al. | |
| 6,506,900 B1 | 1/2003 | Banholzer et al. | |
| 6,537,524 B1* | 3/2003 | Hassan et al. ............. 424/45 |
| 6,777,423 B2 | 8/2004 | Banholzer et al. | |
| 6,908,928 B2 | 6/2005 | Banholzer et al. | |
| 7,309,707 B2* | 12/2007 | Bender et al. ........... 514/291 |
| 7,311,894 B2* | 12/2007 | Schmelzer ............... 424/45 |
| 2002/0183292 A1 | 12/2002 | Pairet et al. | |
| 2002/0193392 A1 | 12/2002 | Schmelzer et al. | |
| 2003/0125350 A1 | 7/2003 | Hassan et al. | |
| 2004/0002510 A1 | 1/2004 | Bender et al. | |
| 2004/0087793 A1 | 5/2004 | Banholzer et al. | |
| 2006/0083692 A1 | 4/2006 | Hassan et al. | |
| 2007/0249656 A1* | 10/2007 | Schmelzer ............... 514/294 |

FOREIGN PATENT DOCUMENTS

| | | |
|---|---|---|
| CA | 2338753 A1 | 2/2000 |
| WO | 0006121 A1 | 2/2000 |
| WO | WO 00/07567 | 2/2000 |
| WO | 0030607 A1 | 6/2000 |
| WO | 0178736 A1 | 10/2001 |
| WO | 0178739 A1 | 10/2001 |
| WO | WO 01/78743 A1 | 10/2001 |
| WO | WO 02/30928 A1 | 4/2002 |
| WO | WO 02/36106 A2 | 5/2002 |
| WO | WO 02/36106 A3 | 5/2002 |
| WO | WO 02/38154 A2 | 5/2002 |

OTHER PUBLICATIONS

Bryn, S., et al: "Review—Pharmaceutical Solids: A Strategic Approach to Regulatory Considerations" Pharmaceutical Research, vol. 12, No. 7, 1995, pp. 945-953.
U.S. Appl. No. 11/765,608, filed Jun. 20, 2007.

* cited by examiner

*Primary Examiner*—Mina Haghighatian
(74) *Attorney, Agent, or Firm*—Michael P. Morris; Mary-Ellen M. Devlin; Wendy A. Petka

(57) ABSTRACT

The invention relates to propellant gas formulations containing suspensions of the crystalline monohydrate of $(1\alpha,2\beta,4\beta,5\alpha,7\beta)$-7-[(hydroxydi-2-thienylacetyl)oxy]-9,9-dimethyl-3-oxa-9-azoniatricyclo[$3.3.1.0^{2,4}$]nonane-bromide.

9 Claims, No Drawings

HFA SUSPENSION FORMULATIONS CONTAINING AN ANTICHOLINERGIC

RELATED APPLICATIONS

This application is a continuation of U.S. application Ser. No. 10/392,559 filed Mar. 20, 2003, now U.S. Pat. No. 7,311,894, which claims priority to German application no. DE 102 14 263.7 filed Mar. 28, 2002 and U.S. provisional application No. 60/386,145 filed Jun. 5, 2002, each of which is herby incorporated by reference in its entirety.

FIELD OF THE INVENTION

The invention relates to pressurised gas preparations for metered-dose aerosols with suspension formulations of the crystalline monohydrate of $(1\alpha,2\beta,4\beta,5\alpha,7\beta)$-7-[(hydroxydi-2-thienylacetyl)oxy]-9,9-dimethyl-3-oxa-9-azoniatricyclo[3.3.1.0$^{2,4}$]nonane-bromide, processes for the preparation thereof and the use thereof for preparing a pharmaceutical composition, particularly for preparing a pharmaceutical composition with an anticholinergic activity.

BACKGROUND TO THE INVENTION

The compound $(1\alpha,2\beta,4\beta,5\alpha,7\beta)$-7-[(hydroxydi-2-thienylacetyl)oxy]-9,9-dimethyl-3-oxa-9-azoniatricyclo [3.3.1.0$^{2,4}$]nonane-bromide, is known from European Patent Application EP 418 716 A1 and has the following chemical structure:

(I)

The compound has valuable pharmacological properties and is known by the name tiotropium bromide (BA679). Tiotropium bromide is a highly effective anticholinergic and can therefore provide therapeutic benefit in the treatment of asthma or COPD (chronic obstructive pulmonary disease).

Tiotropium bromide is preferably administered by inhalation.

The aim of the present invention is to prepare HFA-metered-dose aerosols containing tiotropium bromide as the sole active ingredient in suspended form.

DETAILED DESCRIPTION OF THE INVENTION

It has been found that, depending on the choice of conditions which can be used when purifying the crude product obtained after industrial manufacture, tiotropium bromide occurs in various crystalline modifications.

It has been found that these different modifications can be deliberately produced by selecting the solvents used for the crystallisation as well as by a suitable choice of the process conditions used in the crystallisation process. For the purposes of preparing the formulations according to the invention, crystalline tiotropium bromide monohydrate has proved particularly suitable.

Accordingly, the present invention relates to suspensions of crystalline tiotropium bromide monohydrate in the propellant gases HFA 227 and/or HFA 134a, optionally in admixture with one or more other propellant gases, preferably selected from the group consisting of propane, butane, pentane, dimethylether, $CHClF_2$, $CH_2F_2$, $CF_3CH_3$, isobutane, isopentane and neopentane.

Preferred suspensions according to the invention are those which contain as propellant gas HFA 227 on its own, a mixture of HFA 227 and HFA 134a or HFA 134a on its own. If a mixture of propellant gases HFA 227 and HFA 134a is used in the suspension formulations according to the invention, the weight ratios in which these two propellant gas components are used may be freely selected. If in the suspension formulations according to the invention one or more other propellant gases are used in addition to the propellant gases HFA 227 and/or HFA 134a, selected from the group consisting of propane, butane, pentane, dimethylether, $CHClF_2$, $CH_2F_2$, $CF_3CH_3$, isobutane, isopentane and neopentane, the proportion of this other propellant gas component is preferably less than 50%, preferably less than 40%, more preferably less than 30%.

The suspensions according to the invention preferably contain between 0.001 and 0.8% tiotropium. Suspensions which contain 0.08 to 0.5%, more preferably 0.2 to 0.4% tiotropium are preferred according to the invention.

By tiotropium is meant the free ammonium cation. The propellant gas suspensions according to the invention are characterised in that they contain tiotropium in the form of the crystalline tiotropium bromide monohydrate which is exceptionally suitable for this application. Accordingly, the present invention preferably relates to suspensions which contain between 0.0012 and 1% crystalline tiotropium bromide monohydrate.

Of particular interest according to the invention are suspensions which contain 0.1 to 0.62%, more preferably 0.25 to 0.5% crystalline tiotropium bromide monohydrate.

The percentages specified within the scope of the present invention are always percent by mass. If parts by mass of tiotropium are given in percent by mass, the corresponding values for the crystalline tiotropium bromide monohydrate which is preferably used within the scope of the present invention may be obtained by multiplying by a conversion factor of 1.2495.

In some cases within the scope of the present invention the term suspension formulation may be used instead of the term suspension. The two terms are to be regarded as interchangeable within the scope of the present invention.

The propellant-containing inhalation aerosols or suspension formulations according to the invention may also contain other ingredients such as surface-active agents (surfactants), adjuvants, antioxidants or flavourings.

The surface-active agents (surfactants) which may be contained in the suspensions according to the invention are preferably selected from among Polysorbate 20, Polysorbate 80, Myvacet 9-45, Myvacet 9-08, isopropylmyristate, oleic acid, propyleneglycol, polyethyleneglycol, Brij, ethyloleate, glyceryl trioleate, glyceryl monolaurate, glyceryl monooleate, glyceryl monosterate, glyceryl monoricinoleate, cetylalcohol, sterylalcohol, cetylpyridinium chloride, block polymers, natural oil, ethanol and isopropanol. Of the abovementioned suspension adjuvants Polysorbate 20, Polysorbate 80, Myvacet 9-45, Myvacet 9-08 or isopropylmyristate are preferably used. Myvacet 9-45 or isopropylmyristate are particularly preferred.

Where the suspensions according to the invention contain surfactants, these are preferably present in an amount of 0.0005-1%, more preferably 0.005-0.5%.

The adjuvants optionally contained in the suspensions according to the invention are preferably selected from among alanine, albumin, ascorbic acid, aspartame, betaine, cysteine, phosphoric acid, nitric acid, hydrochloric acid, sulphuric acid and citric acid. Of these, ascorbic acid, phosphoric acid, hydrochloric acid or citric acid are preferred, while hydrochloric acid or citric acid is more preferable.

Where the suspensions according to the invention contain adjuvants, these are preferably present in an amount of 0.0001-1.0%, preferably 0.0005-0.1%, more preferably 0.001-0.01%, while an amount of from 0.001-0.005% is particularly preferred according to the invention.

The antioxidants optionally contained in the suspensions according to the invention are preferably selected from among ascorbic acid, citric acid, sodium edetate, editic acid, tocopherols, butylhydroxytoluene, butylhydroxyanisol and ascorbyl palmitate, of which tocopherols, butylhydroxytoluene, butylhydroxyanisol and ascorbyl palmitate are preferred.

The flavourings which may be contained in the suspensions according to the invention are preferably selected from among peppermint, saccharine, Dentomint®, aspartame and ethereal oils (e.g. cinnamon, aniseed, menthol, camphor), of which peppermint or Dentomint® is particularly preferred.

For administration by inhalation it is necessary to prepare the active substance in finely divided form. The crystalline tiotropium bromide monohydrate which may be obtained as detailed in the experimental section is either ground (micronised or obtained in finely divided form by other technical methods known in principle in the art (such as precipitation and spray drying). Methods of micronising active substances are known in the art. Preferably, after micronisation, the active substance has an average particle size of 0.5 to 10 μm, preferably 1 to 6 μm, more preferably 1.5 to 5 μm. Preferably, at least 50%, more preferably at least 60%, most preferably at least 70% of the particles of active substance have a particle size which is within the ranges specified above. More preferably, at least 80%, most preferably at least 90% of the particles of active substance have a particle size within the ranges specified above.

Surprisingly, it has been found that it is also possible to prepare suspensions which contain, apart from the abovementioned propellant gases, only the active substance and no other additives. Accordingly, in another aspect, the present invention relates to suspensions which contain only the active substance and no other additives.

The suspensions according to the invention may be prepared by methods known in the art. For this the ingredients of the formulation are mixed with the propellant gas or gases (optionally at low temperatures) and transferred into suitable containers.

The propellant gas-containing suspensions according to the invention mentioned above may be administered using inhalers known in the art (pMDIs=pressurised metered dose inhalers). Accordingly, in another aspect, the present invention relates to pharmaceutical compositions in the form of suspensions as hereinbefore described combined with one or more inhalers suitable for administering these suspensions. In addition, the present invention relates to inhalers which are characterised in that they contain the propellant gas-containing suspensions described above according to the invention.

The present invention also relates to containers (e.g. cartridges) which are fitted with a suitable valve and can be used in a suitable inhaler and which contain one of the abovementioned propellant gas-containing suspensions according to the invention. Suitable containers (e.g. cartridges) and methods of filling these cartridges with the propellant gas-containing suspensions according to the invention are known from the prior art.

In view of the pharmaceutical activity of tiotropium the present invention further relates to the use of the suspensions according to the invention for preparing a drug for administration by inhalation or by nasal route, preferably for preparing a drug for the treatment by inhalation or by nasal route of diseases in which anticholinergics may provide a therapeutic benefit.

Most preferably, the invention further relates to the use of the suspensions according to the invention for preparing a pharmaceutical composition for the treatment by inhalation of respiratory complaints, preferably asthma or COPD.

The Examples that follow serve to illustrate the present invention more fully by way of example, without restricting it to their content.

Starting Materials

Crystalline Tiotropium Bromide Monohydrate:

The tiotropium obtained according to EP 418 716 A1 may be used to prepare the crystalline tiotropium bromide monohydrate. This is then reacted as described below. 15.0 kg of tiotropium bromide are added to 25.7 kg of water in a suitable reaction vessel. The mixture is heated to 80-90° C. and stirred at constant temperature until a clear solution is formed. Activated charcoal (0.8 kg), moistened with water, is suspended in 4.4 kg of water, this mixture is added to the solution containing tiotropium bromide and rinsed with 4.3 kg of water. The mixture thus obtained is stirred for at least 15 min. at 80-90° C. and then filtered through a heated filter into an apparatus which has been preheated to an outer temperature of 70° C. The filter is rinsed with 8.6 kg of water. The contents of the apparatus are cooled to a temperature of 20-25° C. at a rate of 3-5° C. every 20 minutes. Using cold water the apparatus is cooled further to 10-15° C. and crystallisation is completed by stirring for at least another hour. The crystals are isolated using a suction filter drier, the crystal slurry isolated is washed with 9 L of cold water (10-15° C.) and cold acetone (10-15° C.). The crystals obtained are dried at 25° C. for 2 hours in a nitrogen current. Yield: 13.4 kg of tiotropium bromide monohydrate (86% of theory).

The tiotropium bromide monohydrate obtainable using the method described above was investigated by DSC (Differential Scanning Calorimetry). The DSC diagram shows two characteristic signals. The first, relatively broad, endothermic signal between 50-120° C. can be attributed to the dehydration of the tiotropium bromide monohydrate into the anhydrous form. The second, relatively sharp, endothermic peak at 230±5° C. can be put down to the melting of the substance. This data was obtained using a Mettler DSC 821 and evaluated using the Mettler STAR software package. The data was recorded at a heating rate of 10 K/min.

The crystalline tiotropium bromide monohydrate was characterised by IR spectroscopy. The data was obtained using a Nicolet FTIR spectrometer and evaluated with the Nicolet OMNIC software package, version 3.1. The measurement was carried out with 2.5 μmol of tiotropium bromide monohydrate in 300 mg of KBr. The following Table shows some of the essential bands of the IR spectrum.

| Wave number (cm$^{-1}$) | Attribution | Type of oscillation |
|---|---|---|
| 3570, 3410 | O—H | elongated oscillation |
| 3105 | Aryl C—H | elongated oscillation |
| 1730 | C═O | elongated oscillation |
| 1260 | Epoxide C—O | elongated oscillation |
| 1035 | Ester C—OC | elongated oscillation |
| 720 | Thiophene | cyclic oscillation |

The monocrystal X-ray structural analysis carried out showed that the crystalline tiotropium bromide monohydrate obtainable by the above process has a simple monoclinic cell with the following dimensions:

a=18.0774 Å, b=11.9711 Å, c=9.9321 Å, β=102.691°, V=2096.96 Å$^3$.

These data were obtained using an AFC7R 4-circuit diffractometer (Rigaku) using monochromatic copper $K_\alpha$ radiation. The structural resolution and refinement of the crystal structure were obtained by direct methods (SHELXS86 Program) and FMLQ-refinement (TeXsan Program).

To prepare the suspensions according to the invention the crystalline tiotropium bromide monohydrate obtainable by the above process is micronised by methods known per se in the art, to prepare the active substance in the form of the average particle size which corresponds to the specifications according to the invention.

A method of determining the average particle size of the active substance will now be described.

Determining the Particle Size of Micronised Tiotropium Bromide Monohydrate:

Measuring Equipment and Settings:

The equipment is operated according to the manufacturer's instructions.

| | |
|---|---|
| Measuring equipment: | HELOS Laser diffraction spectrometer, SympaTec |
| Dispersing unit: | RODOS dry disperser with suction funnel, SympaTec |
| Sample quantity: | 50 mg-400 mg |
| Product feed: | Vibri Vibrating channel, Messrs. Sympatec |
| Frequency of vibrating channel: | 40 rising to 100% |
| Duration of sample feed: | 15 to 25 sec. (in the case of 200 mg) |
| Focal length: | 100 mm (measuring range: 0.9-175 μm) |
| Measuring time: | about 15 s (in the case of 200 mg) |
| Cycle time: | 20 ms |
| Start/stop at: | 1% on channel 28 |
| Dispersing gas: | compressed air |
| Pressure: | 3 bar |
| Vacuum: | maximum |
| Evaluation method: | HRLD |

Sample Preparation/Product Feed:

About 200 mg of the test substance are weighed onto a piece of card. Using another piece of card all the larger lumps are broken up. The powder is then sprinkled finely over the front half of the vibrating channel (starting about 1 cm from the front edge). After the start of the measurement the frequency of the vibrating channel is varied from about 40% up to 100% (towards the end of the measurement). The sample should be fed in as continuously as possible. However, the quantity of product should not be too great, so as to ensure adequate dispersal.

The time taken to feed in the entire 200 mg sample is about 15 to 25 sec., for example.

EXAMPLES OF FORMULATIONS

Suspensions containing other ingredients in addition to active substance and propellant gas:

| | | |
|---|---|---|
| a) | 0.02% | Tiotropium* |
| | 0.20% | Polysorbate 20 |
| | 99.78% | HFA 227 |
| b) | 0.02% | Tiotropium* |
| | 1.00% | Isopropylmyristate |
| | 98.98% | HFA 227 |
| c) | 0.02% | Tiotropium* |
| | 0.3% | Myvacet 9-45 |
| | 99.68% | HFA 227 |
| d) | 0.04% | Tiotropium* |
| | 1.00% | Myvacet 9-08 |
| | 98.96% | HFA 227 |
| e) | 0.04% | Tiotropium* |
| | 0.04% | Polysorbate 80 |
| | 99.92% | HFA 227 |
| f) | 0.04% | Tiotropium* |
| | 0.005% | Oleic acid |
| | 99.955% | HFA 227 |
| g) | 0.02% | Tiotropium* |
| | 0.1% | Myvacet 9-45 |
| | 60.00% | HFA 227 |
| | 39.88% | HFA 134a |
| h) | 0.02% | Tiotropium* |
| | 0.30% | Isopropylmyristate |
| | 20.00% | HFA 227 |
| | 79.68% | HFA 134a |
| i) | 0.02% | Tiotropium* |
| | 0.01% | Oleic acid |
| | 60.00% | HFA 227 |
| | 39.97% | HFA 134a |

*used in the form of the tiotropium bromide monohydrate (conversion factor 1.2495)

Suspensions containing only active substance and propellant gas:

| | | |
|---|---|---|
| j) | 0.02% | Tiotropium* |
| | 99.98% | HFA 227 |
| k) | 0.02% | Tiotropium* |
| | 99.98% | HFA 134a |
| l) | 0.04% | Tiotropium* |
| | 99.96% | HFA 227 |
| m) | 0.04% | Tiotropium* |
| | 99.96% | HFA 134a |
| n) | 0.02% | Tiotropium* |
| | 20.00% | HFA 227 |
| | 79.98% | HFA 134a |
| o) | 0.02% | Tiotropium* |
| | 60.00% | HFA 227 |
| | 39.98% | HFA 134a |
| p) | 0.04% | Tiotropium* |
| | 40.00% | HFA 227 |
| | 59.96% | HFA 134a |
| q) | 0.04% | Tiotropium* |
| | 80.00% | HFA 227 |
| | 19.96% | HFA 134a |

*used in the form of the tiotropium bromide monohydrate (conversion factor 1.2495)

What is claimed is:

1. A suspension of (1) crystalline tiotropium bromide monohydrate in propellant gases HFA 227 and/or HFA 134a, optionally in admixture with one or more other propellant gases selected from the group consisting of propane, butane, pentane, dimethylether, $CHClF_2$, $CH_2F_2$, $CF_3CH_3$, isobutane, isopentane and neopentane, wherein the crystalline tiotropium bromide monohydrate has a simple monoclinic cell with the dimensions a=18.0774 Å, b=11.9711 Å, c=9.9321 Å, β=102.691°, and V=2096.96 Å$^3$ and (2) one or more adjuvants.

2. The suspension according to claim 1, wherein The adjuvant is selected from the group consisting of alanine, albumin, ascorbic acid, aspartame, betaine, cysteine, phosphoric acid, nitric acid, hydrochloric acid, sulphuric acid and citric acid.

3. The suspension according to claim 1, further containing surfactants, antioxidants, flavourings or combinations thereof.

4. The suspension according to claim 3, wherein the surfactant is one or more compounds selected from the group consisting of Polysorbate 20, Polysorbate 80, Myvacet 9-45, Myvacet 9-08, isopropylmyristate, oleic acid, propyleneglycol, polyethyleneglycol, Brij, ethyl oleate, glyceryl trioleate, glyceryl monolaurate, glyceryl monooleate, glyceryl monosterate, glyceryl monoricinoleate, cetylalcohol, sterylalcohol, cetylpyridinium chloride, block polymers, natural oil, ethanol and isopropanol.

5. The suspension according to claim 3, wherein the antioxidant is one or more compounds selected from the group consisting of ascorbic acid, citric acid, sodium edetate, editic acid, tocopherols, butylhydroxytoluene, butylhydroxyanisol and ascorbyl palmitate.

6. The suspension according to claim 1, wherein the amount of tiotropium bromide is between 0.001 and 0.8%.

7. The suspension according to claim 1, wherein the propellant gas is HFA 227.

8. The suspension according to claim 1, wherein the propellant gas is HFA 134a.

9. The suspension according to claim 1, wherein the propellant gas is a mixture of HFA 227 and HFA 134a.

* * * * *